United States Patent [19]

Nieuwkamp

[11] 4,279,820
[45] Jul. 21, 1981

[54] PROCESS FOR PREPARING 2-PYRROLIDONES

[75] Inventor: Johannes G. M. Nieuwkamp, Limbricht, Netherlands

[73] Assignee: Stamicarbon B.V., Geleen, Netherlands

[21] Appl. No.: 136,115

[22] Filed: Mar. 27, 1980

[30] Foreign Application Priority Data

Apr. 1, 1979 [NL] Netherlands ................ 7902537

[51] Int. Cl.$^3$ .................................... C07D 207/38
[52] U.S. Cl. ................................... 260/326.5 FM
[58] Field of Search ......................... 260/326.5 FM

[56] References Cited

U.S. PATENT DOCUMENTS

| | | | |
|---|---|---|---|
| 3,853,922 | 12/1974 | Yamaguchi | 252/472 |
| 3,884,936 | 5/1975 | Hollstein | 260/326.5 FM |

Primary Examiner—Anton H. Sutto
Assistant Examiner—D. B. Springer
Attorney, Agent, or Firm—Cushman, Darby & Cushman

[57] ABSTRACT

2-pyrrolidones are prepared by hydrogenating a succinonitrile in the liquid phase in the presence of ammonia by passing an ammoniacal solution of a succinonitrile over a fixed bed catalyst, particularly of the trickle-phase type, in which the catalyst is nickel on an alkaline support such as calcium hydroxide or calcium carbonate. Attractive yields are achieved without the expense of filtering off and separating used catalyst as in prior procedures.

10 Claims, No Drawings

PROCESS FOR PREPARING 2-PYRROLIDONES

The present invention relates to a process for the preparation of 2-pyrrolidone or a C-substituted 2-pyrrolidone by subjecting a non-substituted or substituted succinonitrile to catalytic hydrogenation in the liquid phase, in the presence of ammonia, treating the resulting hydrogenated product with water and recovering the resulting 2-pyrrolidone product.

This general type of process is already described in U.S. Pat. No. 4,123,438 and can be carried out to give a good yield by suspending the catalyst required for the hydrogenation, typically a Raney nickel, in the liquid phase. However, in this process, the removal of the catalyst after completion of the hydrogenation, e.g., by filtration (see col. 2, lines 56-57), is a rather costly operation.

A method of effecting this hydrogenation has now been found and is herein disclosed which also gives good yields together with a less costly operation for the separation of the catalyst from the reaction mixture.

The process according to the present invention includes preparing 2-pyrrolidone or a C-substituted 2-pyrrolidone by subjecting an optionally substituted succinonitrile to catalytic hydrogenation in the liquid phase, in the presence of ammonia, and treating the resulting hydrogenated product with water, and is characterized in that the hydrogenation is effected with a catalyst in the form of a fixed bed, the catalyst specifically being nickel on an alkaline carrier.

The resulting 2-pyrrolidones are themselves known and are useful in preparing polyamides, like nylon-4, and as a feedstock for preparing (poly)N-vinyl pyrrolidone.

Alkaline carriers that may be used in the process according to the present invention are, for instance, the oxides and hydroxides of metals such as alkaline earth metals, alkali metals, thorium and zirconium and the salts which these oxides or hydroxides can form with weak inorganic acids, e.g., carbon dioxide. Examples of suitable carrier materials include magnesium oxide, magnesium hydroxide, magnesium carbonate, barium hydroxide, barium carbonate, calcium bicarbonate, calcium hydroxide and calcium carbonate. Mixtures of these alkaline carrier materials may be used as well. Very suitable as carriers are one or more of the compounds selected from the group consisting of calcium hydroxide, calcium carbonate, magnesium oxide, magnesium hydroxide, and magnesium carbonate. The nature of the carrier for the catalyst is important as previously used catalysts, for instance, alumina and silica, do not give yields as high as those of the invention.

The nickel content of the catalyst is typically in the range of 5 to 80% by weight and preferably has a nickel content of 10–60% wt.

The nickel may be applied to the carrier by conventional means, for instance, the method in which the carrier material is impregnated with a solution of a nickel salt, after which the solvent is evaporated, and the nickel salt, if necessary subsequent to having been decomposed to nickel oxide, is reduced to metallic nickel. According to another known method the catalyst can be prepared by precipitating, at a temperature between, for example, 60° and 100° C., nickel hydroxide and/or nickel carbonate from an aqueous solution of a nickel salt, for instance, nickel nitrate, nickel sulfate, nickel chloride, nickel acetate, or nickel formiate, with a concentration of, for instance, between 0.5 and 5 moles of nickel salt per liter, with the aid of a hydroxide and/or carbonate of an alkali metal or ammonium, or with the aid of a urea solution. The resulting precipitate can then be mixed with the carrier material. Preferably, the carrier material is already present in the nickel salt solution when the nickel hydroxide or nickel carbonate is precipitated. The nickel salt in the resulting mixture is then reduced to metallic nickel regardless of whether it has been decomposed to nickel oxide.

The quantity of ammonia that should be present in the liquid phase per gram of succinonitrile to be converted may vary within certain practical limits, for instance, between 0.5 and 25 grams of ammonia per gram of succinonitrile to be converted. In addition to ammonia, an additional solvent may be present, for instance, toluene, xylene, tetrahydrofuran, pyrrolidone or pyridine, but the presence of an additional solvent does not result in any particular advantage. Preferably, a solution in liquid ammonia of the succinonitrile to be converted is contacted directly with the fixed catalyst bed.

The process according to the present invention can be carried out at various partial hydrogen pressures, depending on the nature of the reactants and the pressures employed. For instance, a partial hydrogen pressure between 100 and 35,000 kPa may be used. In practice, a partial hydrogen pressure of 500–10,000 kPa is preferred.

In the process according to the present invention the hydrogenation can be carried out at various temperatures, for instance, a temperature between 40° and 150° C., however, preferably a temperature between 50° and 130° C. is used.

The hydrogenation according to the present invention can be carried out very suitably in a socalled "trickle-phase" reactor in which a solution of the succinonitrile in liquid ammonia flows across the fixed catalyst bed—consisting of a particulate catalyst material in the form of tablets, granules, extrudate, or pellets—under the influence of gravity, while the hydrogen or the hydrogen-containing gas is passed across the catalyst bed either co-currently or counter-currently. The specific loading of the catalyst may then have any of various values, for example, between 0.1 and 25 liters of liquid per liter of catalyst (bulk density) and per hour, and preferably between 0.5 and 10 liters of liquid per liter of catalyst and per hour.

After the hydrogenation of the succinonitrile, all or part of the ammonia may be removed from the resulting reaction mixture, for example, by evaporation. The treatment of the hydrogenated product with water may be carried out in the presence as well as in the absence of ammonia. As in the known process mentioned above, various temperatures may be applied in this water treatment, for instance, a temperature between 150° and 300° C. is fully acceptable. Also, the quantity may be varied, as in the known process, for instance, between the amount stoichiometrically required up to 20 moles per mole of succinonitrile.

The starting product used in the process according to the invention may be succinonitrile itself or a substituted succinonitrile, for instance, a succinonitrile substituted with an alkyl group containing from 1 to 4 carbon atoms substituted in the second or third positions, or both.

The process according to the present invention will be elucidated in the following examples. Unless otherwise indicated, all parts and percentages are by weight.

EXAMPLE 1

Catalyst Preparation

Nickel nitrate (2,000 g, $Ni(NO_3)_2.6H_2O$) was dissolved in 4 liters of distilled water. In the resulting solution calcium hydroxide (270 g, made by J. T. Baker chemicals) was suspended. The suspension was heated to 90° C. with stirring, after which in about 1 hour's time a solution of anhydrous sodium carbonate (850 g) in 4 liters of distilled water was added to the suspension. The resulting precipitate was separated off by filtration and washed with a solution of calcium hydroxide in distilled water saturated at room temperature, until the washing water could no longer be demonstrated to contain sodium by the zinc uranyl nitrate method. Thereafter, the catalyst mass was dried in air for 24 hours at 120° C.

When analyzed, the mass obtained in this manner was found to consist of 32.4% by weight of nickel in the form of nickel carbonate and nickel hydroxide on a mixture of calcium hydroxide and calcium carbonate (weight ratio about 1:1).

After grinding, the mass was mixed with 2% wt. of graphite (as lubricant) and compressed to tablets having a diameter and length of about 3 mm.

Pyrrolidone Preparation

Per hour, an amount of succinonitrile (0.1 kg) was dissolved in liquid ammonia (1.25 kg) at an elevated pressure in a mixer heated at 80° C., after which the resulting solution was pumped into the top of a vertically disposed metal tubular reactor (length 1.5 meters, internal diameter 2.54 centimeters).

The reactor contained a bottom layer of 600 milliliters of catalyst, and a top layer consisting of 75 milliliters of inert packing material (protruded metal packing, dimensions 0.16 by 0.16 cm). Before the start of the experiment, the catalyst had been activated by passing nitrogen across it, for 10 hours and at 200° C., and then hydrogen, for 30 hours and at 335° C.

At the same time as the liquid ammonia/succinonitrile solution was introduced into the top of the tubular reactor, hydrogen was also introduced into the top by means of a compressor, at the rate of 930 liters (0° C. and 100 kPa) per hour. The hydrogen partial pressure in the reactor was maintained at 4000 kPa. (The total pressure was 10,000 kPa.) The temperature in the reactor was maintained at 85° C. with the use of a heating jacket.

The resulting reaction mixture was discharged from the reactor at the bottom, cooled to 40° C., and separated under pressure in a separator into liquid and gas. Thereafter, the ammonia was removed from the resulting liquid in an expansion vessel operated at atmospheric pressure. After 25 hours operation, the next 2 hours product thus obtained was collected. A 2-gram sample of this product (208 grams) was analyzed by gas chromatography, which showed that the starting product was no longer present. While being stirred, the remaining amount of the collected product was heated for 0.5 hour at 210° C. in a 1-liter autoclave, together with 200 grams of water. After cooling, the hydrolyzed product was analyzed by gas chromatography. This showed 185 grams of pyrrolidone were formed. Calculated in relation to the amount of succinonitrile introduced, this means that the efficiency was 87%. By distillation of the hydrolysis mixture at reduced pressure, virtually pure (99% purity) pyrrolidone can be recovered, which can be further purified, if so desired, by distillation over an acid, for instance, sulfuric acid, and/or an alkali, for instance sodium hydroxide.

When the experiment was repeated with a commercially obtainable nickel catalyst (50% wt. nickel on an $Al_2O_3$ carrier) under otherwise equal conditions, the efficiency was only 75%.

EXAMPLE 2

Catalyst Preparation

Nickel nitrate (2000 g, $Ni(NO_3)_2.6H_2O$) was dissolved in 4 liters of distilled water. In the resulting solution powdery magnesium oxide (270 g, made by Saline Luneburg) was suspended. The suspension was heated to 90° C. while being stirred, after which in about 1 hour's time a solution of anhydrous sodium carbonate (850 g) in 4 liters of distilled water was added to the suspension. The resulting precipitate was separated off by filtration and washed with distilled water until the washing water could no longer be demonstrated to contain sodium by the zinc uranyl nitrate method. Thereafter, the catalyst mass was dried in air for 24 hours at 120° C.

When analyzed, the mass obtained in this way proved to consist of 32.7% by weight of nickel in the form of nickel carbonate and nickel hydroxide on magnesium hydroxide.

After grinding, the mass was mixed with 2% by weight of graphite (as a lubricant) and compressed into tablets having a diameter and length of about 3 mm.

Pyrrolidone Preparation

Per hour, an amount of succinonitrile (225 g) was dissolved in liquid ammonia (3.1 kg) at elevated pressure in a mixer heated to 97° C., after which the resulting solution was pumped into the top of a vertically disposed metal tubular reactor (length 1.5 meters, internal diameter 2.5 centimeters).

The reactor contained a layer of 600 milliliters of catalyst, with, on top of it, a layer of 75 milliliters of inert packing material (protruded metal packing, dimensions 0.16 by 0.16 cm). Before the start of the experiment, the catalyst had been activated by passing nitrogen across it, for 10 hours and at 200° C., and then hydrogen, for 30 hours and at 335° C. Together with the solution of succinonitrile dissolved in ammonia.

Hydrogen was introduced into the top of the tubular reactor by means of a compressor, at the rate of 1200 liters (0° C. and 100 kPa) per hour. The partial hydrogen pressure in the reactor was kept at 3500 kPa. (The total pressure was 10,000 kPa.) The temperature in the reactor was maintained at 100° C. with the use of a heating jacket.

The resulting reaction mixture was discharged from the reactor at the bottom, cooled to 40° C., and separated under pressure in a separator into liquid and gas. Thereafter, the ammonia was removed from the resulting liquid in an expansion vessel operated at atmospheric pressure. After 25 hours operation, the next 2 hours product thus obtained was collected. A 2-gram sample of this product (245 grams) was analyzed by gas chromatography, which showed that 97% of the starting product had been converted. While being stirred, the remaining amount of the collected product was heated for 45 minutes at 210° C. in a 1-liter autoclave, together with 250 grams of water. After cooling, the hydrolyzed product was analyzed by gas chromatography. This showed that 197 grams of pyrrolidone were formed.

Calculated with respect to the amount of succinonitrile converted, this means that the efficiency was 85%. By distillation of the hydrolysis mixture at reduced pressure, virtually pure (99% purity) pyrrolidone can be recovered, which can be further purified, if so desired, by distillation over an acid, for instance, sulfuric acid, and/or alkali, for instance sodium hydroxide.

When this experiment was repeated with a commercially obtainable nickel catalyst (50% wt. nickel on an $Al_2O_3$ carrier) under otherwise equal conditions, the efficiency was only 75%.

What is claimed is:

1. In a process for preparing 2-pyrrolidone comprising the steps of catalytically hydrogenating succinonitrile in the liquid phase, in the presence of ammonia, and then hydrolyzing the resulting reaciton product with water and thereafter recovering the 2-pyrrolidone product, the improvement consisting essentially of conducting the hydrogenation step at a temperature between about 40° to 150° C. by passing succinonitrile, together with a stream of hydrogen at a partial hydrogen pressure of 100 to 35,000 kPa, through a fixed bed of nickel catalyst having a nickel content in the amount of from 5 to about 80% by weight, said catalyst carried on an alkaline carrier that is the oxide, hydroxide or carbonate of an alkaline earth metal, an alkali metal, thorium, zirconium or mixtures thereof.

2. The process according to claim 1, wherein said alkaline carrier is selected from the group consisting of calcium hydroxide, calcium carbonate, magnesium oxide, magnesium hydroxide, magnesium carbonate and mixtures thereof.

3. The process according to claims 1 or 2, wherein the nickel content of the catalyst is from 10 to 60% by weight.

4. The process according to claims 1 or 2, wherein during the hydrogenation from 0.5 to 25 grams of ammonia is used per gram of succinonitrile to be hydrogenated.

5. The process according to claims 1 or 2, wherein the hydrogenation is conducted at a partial hydrogen pressure between 500 and 10,000 kPa.

6. The process according to claims 1 or 2, wherein the hydrogenation is conducted at a temperature between about 50° and about 130° C.

7. The process according to claims 1 or 2, wherein the hydrogenation is conducted in a trickle-phase reactor.

8. The process according to claims 1 or 2, wherein the specific catalyst loading for said hydrogenation reaction is between about 0.5 and 10 liters of liquid per liter of catalyst per hour.

9. In a process for preparing 2-pyrrolidone or a 2-pyrrolidone have a $C_1$–$C_4$ alkyl substituent on at least one carbon atom thereof comprising the steps of catalytically hydrogenating succinonitrile or a correspondingly alkylsubstituted succinonitrile, in the presence of ammonia, and then hydrolyzing the resulting reaction product with water and thereafter recovering the 2-pyrroidone product, the improvement consisting essentially in conducting the hydrogenation step by:
(1) passing the succinonitrile, together with a stream of hydrogen, through a fixed catalyst bed,
(2) said catalyst having a nickel content of about 10 to about 60% by weight and held on an alkaline carrier material selected from the group consisting of calcium hydroxide, calcium carbonate, magnesium oxide, magnesium hydroxide, magnesium carbonate and mixtures thereof,
(3) at a temperature of between about 50° and 130° C.,
(4) at a catalyst loading of between about 0.5 and about 10 liters of liquid per liter of catalyst per hour and
(5) at a partial hydrogen pressure of 100 to 35,000 kPa.

10. The process according to claim 9 wherein the partial hydrogen pressure is from 500 to 10,000 kPa.

* * * * *